United States Patent [19]
Davis-Harris

[11] Patent Number: 6,058,943
[45] Date of Patent: May 9, 2000

[54] FORMULATION AND METHOD FOR SMOOTHING AND WAVING MULTI-TEXTURED HAIR

[76] Inventor: Pamela Davis-Harris, 7139 Highway 85, #286, Riverdale, Ga. 30274

[21] Appl. No.: 09/356,731

[22] Filed: Jul. 18, 1999

[51] Int. Cl.[7] .................................................. A45D 7/04
[52] U.S. Cl. ............................................................ 132/205
[58] Field of Search ................................... 132/205, 204, 132/203, 207

[56] References Cited

U.S. PATENT DOCUMENTS

| | | | |
|---|---|---|---|
| 2,624,347 | 1/1953 | Melaro | 132/205 |
| 4,134,411 | 1/1979 | Yamazaki | 132/205 |
| 4,883,657 | 11/1989 | Williams et al. | 132/205 |
| 4,885,160 | 12/1989 | Williams et al. | 132/205 |
| 4,982,749 | 1/1991 | Baker et al. | 132/205 |
| 5,060,680 | 10/1991 | Akhtar | 132/205 |
| 5,476,650 | 12/1995 | Patel | 132/204 |
| 5,617,883 | 4/1997 | Savaides et al. | 132/205 |
| 5,655,552 | 8/1997 | Somain | 132/205 |

*Primary Examiner*—Todd E. Manahan
*Attorney, Agent, or Firm*—Herbert M. Hanegan; J. Rodgers Lunsford, III; Charles L. Warner, II

[57] ABSTRACT

The present invention provides a process by which smoothness, body and a permanent wave pattern can be imparted to multi-textured hair of all types, from hair having an excessively tightly curled appearance, such as Negroid hair, to hair having a straight appearance, such as Caucasian hair, with substantially less damage to the hair. The process of the present invention uniquely combines the use of two hair structure altering chemicals—an alkaline hydroxide (such as sodium hydroxide) and a thioglycolate reducing agent (preferably ammonium thioglycolate)—to harmoniously bring about a desired wave pattern in the hair. Using the Wave Balance Scale (a hair reference scale) of the present invention, a sodium hydroxide formulation is chosen based on the type and natural curl level of the hair. The sodium hydroxide formulation is applied to the hair for a time sufficient to relax the natural curl in the hair by breaking some of the sulfide bonds in the hair. Then, after rinsing but prior to any neutralization, the ammonium thioglycolate formulation is applied to the hair and the hair is placed on curling rods for a time sufficient to rearrange the wave pattern of the relaxed hair. The hair is then rinsed and neutralized, while still rodded, for a time sufficient to lock in the new wave pattern by reforming the sulfide bond linkages. After neutralization, the hair can be shampooed, conditioned and styled either curly or straight as desired by the patron.

20 Claims, 1 Drawing Sheet

FORMULATION AND METHOD FOR SMOOTHING AND WAVING MULTI-TEXTURED HAIR

BACKGROUND OF THE INVENTION

1. Field of the Invention

The present invention is directed to providing a process for imparting smoothness, body and a permanent wave pattern to hair of varying natural curl levels, particularly multi-textured hair. More specifically, the present invention is directed to a multi-step hair treatment process whereby an alkaline hydroxide (preferably sodium hydroxide) is first used to smoothen naturally curly hair, then, prior to neutralization, a thioglycolate reducing agent (preferably ammonium thioglycolate) is used to create a new wave pattern in the hair.

2. Description of the Relevant Art

Conventional hair treatment products based upon compositions containing thioglycolates, sulfites, or alkali metal hydroxides, such as sodium hydroxides, have been widely used to permanently straighten tightly curled hair, especially to straighten the hair of people of African descent. Of these products, the thioglycolate compositions and the sulfite compositions which have been commercially marketed have been relatively ineffective, with the hair in many cases reverting at least partially to the original unstraight form. While very effective in producing the desired straightening effect, sodium hydroxide compositions are very harsh to both the scalp and the hair, and the use of such compositions has resulted in numerous instances of scalp irritation and/or burning, and has also resulted in a substantial reduction in the strength of the treated hair, and even, in some instances, considerable hair breakage and loss.

While thioglycolate compositions have been relatively ineffective in straightening tightly curled hair, they have been very effective in and are widely used for, adding curl or permanent waves to straight hair, such as Caucasian hair. However, because the wave imparted by the thioglycolate compositions relaxes over time, these products must be repeatedly used on naturally straight hair. This recurring use and, from time to time, overuse, can cause the hair to become frizzy and damaged.

While products such as those mentioned above have been formulated for tightly curled and straight hair, there has not previously been much attention given to the special needs of multi-textured hair, that is, hair that is a combination of frizzy, straight, and curly.

Multi-textured hair, to which the present invention is particularly directed, when processed with a conventional chemical straightening treatment, is left straight and limp. When processed with a conventional texturizing treatment, such as that disclosed in U.S. Pat. No. 4,361,157, it is still left with an uncontrolled curl pattern and little body. When processed (wrapped or rodded) as a regular cold body wave, the hair is left with more frizz. Multi-textured hair types can be found in all races, in the descendants of Caucasians, Indians, Asians and Africans. The process of the present invention allows one to understand the general make-up of hair and the link which ties all hair types together, thus allowing the stylist to work on all hair textures using a unique combination of chemical hair treatments.

Numerous U.S. Patents are directed to hair straightening and hair waving. Patents with some relevance to the subject matter of the present invention include the following:

U.S. Pat. No. 4,361,157 describes a method for producing waves in tightly curled hair by a process of applying a relaxer followed by a neutralizer-shampoo after combing.

U.S. Pat. No. 4,793,994 teaches an aqueous relaxing composition using N-alkyl lactams and thioglycolate acid.

U.S. Pat. No. 5,241,973 describes an improved cold wave formulation using polymeric mixed disulfides.

U.S. Pat. No. 4,982,750 describes a method for relaxing and recurring tightly curled or kinked hair using monoethanolamine thioglycolate and a heat-generating composition.

U.S. Pat. Nos. 4,303,085 and 4,314,572 describe the use of guanidine hydroxides to permanently alter hair structure.

None of the cited patents teach the combination of the two separate processes of sodium hydroxide straightening with ammonium thioglycolate waving in one system, nor do they teach sodium hydroxide relaxation followed by a process other than neutralization.

SUMMARY OF THE INVENTION

The present invention provides a process by which smoothness, body and a permanent wave pattern can be imparted to hair of all types, particularly multi-textured hair, as well as hair having an excessively tightly curled appearance, such as Negroid hair and hair having a relatively straight appearance, such as Spanish or Caucasian hair, with substantially less damage to the hair. The process of the present invention uniquely combines the use of two hair structure altering chemicals—an alkaline hydroxide (preferably sodium hydroxide) and a thioglycolate reducing agent (preferably ammonium thioglycolate)—to harmoniously bring about a desired wave pattern in the hair. Using the Wave Balance Scale (a hair reference scale) of the present invention, a sodium hydroxide formulation is chosen based on the type and natural curl level of the hair. The sodium hydroxide formulation, containing a lower level of sodium hydroxide than most conventional straightening products, is applied to the hair for a time sufficient to relax the natural curl in the hair by breaking some of the sulfide bonds in the hair. Then, after rinsing but prior to any neutralization, an ammonium thioglycolate formulation, containing a lower level of ammonium thioglycolate than most conventional waving products, is applied to the hair and the hair is placed on curling rods for a time sufficient to rearrange the wave pattern of the relaxed hair. The hair is then rinsed and neutralized, preferably with a sodium bromate composition while still rodded, for a time sufficient to lock in the new wave pattern by reforming the sulfide bond linkages. After neutralization, the hair can be shampooed, conditioned and styled either curly or straight as desired by the patron.

DESCRIPTION OF THE PREFERRED EMBODIMENTS

Figure 1:
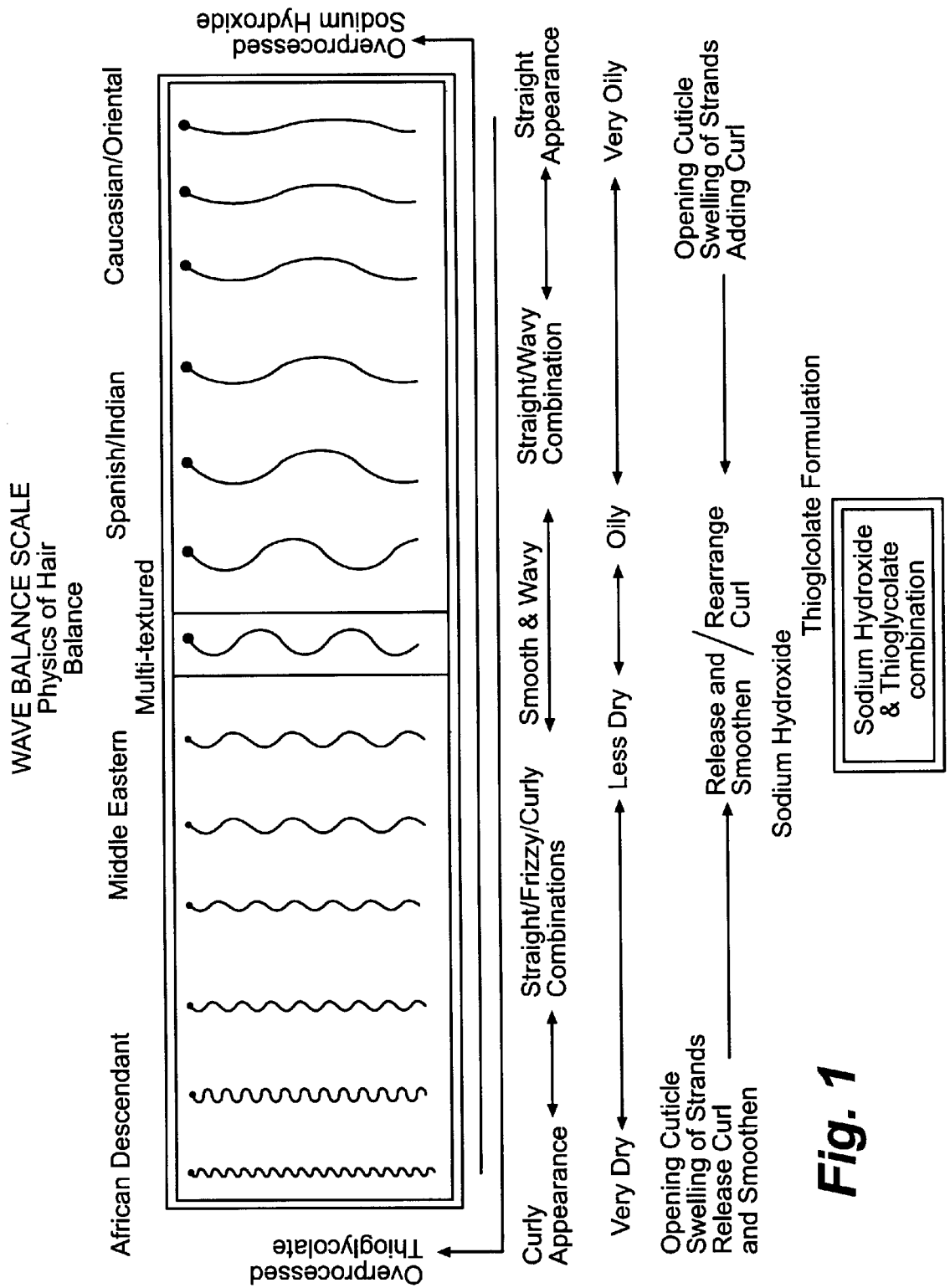
FIG. 1 is a rendition of the Wave Balance Scale of the present invention which shows the common link between all hair types and which can be used to identify the appropriate sodium hydroxide formulation and ammonium thioglycolate formulation for use in the process of the present invention based on the level of natural curl or wave in the subject hair.

The sodium hydroxide formulations of the present invention allow a practitioner to bring out only the desired wave pattern in each texture of naturally tightly curled hair or any multi-textured hair that is frizzy, by not completely destroying the cystine bonds in the hair. The lower level of sodium hydroxide (about 0.5% to about 1.85% NaOH versus about 2% to about 4% in conventional products) in the formulations smooths the hair out, but leaves enough cystine bonds in the hair to allow use of the thioglycolate formulation causing less damage and irritation to the hair and scalp. A critical factor in this process is that neutralization does not take place until the hair has been wrapped, or rodded, in the thioglycolate, and the desired wave pattern has been achieved. The bonds must not be neutralized after smoothing takes place unless body waving is not desired. All prior art relaxer processes using sodium hydroxide require neutralization of the hair after application of the sodium hydroxide and before further processing of the hair. The process of the present invention is unique in that the ammonium thioglycolate is applied to the relaxed hair before neutralization, and thus before the cystine bonds are reformed in the hair, thus allowing the hair to be given smoothness and a new permanent wave pattern which are both then locked into the hair in the neutralization step. If smoothing is all that is desired, then a neutralizing shampoo is used after smoothing and no body wave (ammonium thioglycolate) treatment is performed.

The understanding of hair dynamics, particularly those relating to the hair of people of African descent and to multi-textured hair, is still developing. The Wave Balance Scale of FIG. 1 teaches that the hair of all races is connected by the common thread of wave level. The Wave Balance Scale was created to establish a balanced point of leaving wave in, or adding wave to the hair. The concept, is surprisingly simple—one adds more wave, one releases wave. Conventional treatments for people with tightly curled hair, such as those of African descent, release far too much curl. The word "perm" comes from permanent, and the way the hair appears when it is wet, indicates its true condition. Naturally curly hair, after treatment with conventional curl relaxing processes, appears totally straight when wet. However, when the hair is wet, the wave should be left in the hair and the blown dry, or set look, is what should appear straight. Therefore, chemicals should be made to smoothen the hair without completely destroying the bonds, leaving the hair with strength and elasticity, swelling the cuticle and not thinning it out. The process of the present invention achieves this result by not over-relaxing the hair during the sodium hydroxide relaxation step and by rearranging the natural wave pattern, prior to neutralization, in the ammonium thioglycolate waving step. The present invention utilizes several formulations containing different levels of sodium hydroxide, and different levels of ammonium thioglycolate, keyed to the different hair types of the Wave Balance Scale, to smoothen the hair and rearrange the bond linkages to achieve a looser and fuller permanent wave pattern with body and bounce. The thioglycolate is formulated in a mild cold wave formula so as to put back a desired wave or curl pattern, without making the hair too curly or frizzy again, but permanently waving the hair of all races of people. The hair can now be worn roller set, straight when blow dried, or in a curly style when left to dry naturally, without being frizzy, thus leaving body and bounce in each individual head of hair and leaving the hair in a much healthier state.

As one can see from the depictions of hair at the two ends of the Wave Balance Scale of FIG. 1, the constant use of conventional chemical straighteners leaves naturally tightly curled hair totally limp, with no elasticity and in a fractured, unhealthy state. At the other end of the spectrum, overprocessing with conventional thioglycolate-based cold wave treatments leaves naturally straight hair frizzy, fractured, and virtually unmanageable. The process of the present invention uses lower levels of each of these active ingredients than are found in conventional formulations for straightening or waving hair, respectively, and combines the two treatments in one process for optimal results, something believed to have never been done before.

In the process of the present invention, the subject hair is examined to determine the type of hair and the level of natural curl in the hair in relation to the Wave Balance Scale of FIG. 1. Once it is determined where the hair falls on the Wave Balance Scale, the appropriate sodium hydroxide and ammonium thioglycolate formulations can be selected for treating the subject hair. If the hair is tightly curled and as such falls under "African Descendant" on the Wave Balance Scale, the formulations containing the highest levels of sodium hydroxide and ammonium thioglycolate, respectively, would be used. Conversely, if the subject hair fell on the Caucasian/Oriental end of the Wave Balance Scale, formulations containing the lowest levels of sodium hydroxide and ammonium thioglycolate (in some instances, no sodium hydroxide formulation would be required, only a waving composition containing one of the lower levels of ammonium thioglycolate) would need to be used.

In the process of the present invention, an aqueous alkaline relaxant composition containing an alkaline hydroxide reducing agent is applied to the hair in a substantially conventional manner. Preferably, the alkaline hydroxide reducing agent is an alkali metal hydroxide and most preferably, the alkali metal hydroxide is sodium hydroxide. The aqueous alkaline relaxant composition is comprised predominantly of water and may contain other ingredients, in addition to the active ingredient, such as are found in conventional straightening and relaxing compositions. Consequently, the aqueous alkaline relaxant composition may include, in addition to water and sodium hydroxide, petrolatum, and other buffering, emulsifying, and process enhancing components such as are known in the art. For tightly curled hair, such as might correspond to African descendant hair on the Wave Balance Scale or another hair reference scale, the aqueous alkaline relaxant composition used would contain from about 0.5% to about 1.85% sodium hydroxide. For less tightly curled and somewhat smoother hair, such as might correspond to Middle Eastern hair on the Wave Balance Scale, the aqueous alkaline relaxant composition used would contain from about 0.5% to about 1.65% sodium hydroxide. For more loosely curled and even straighter hair, such as might correspond to Spanish/Indian hair on the Wave Balance Scale, the aqueous alkaline relaxant composition used would contain from about 0.5% to about 1.45% sodium hydroxide. For hair with only a small amount of curl, such as might correspond to Caucasian/Oriental hair on the Wave Balance Scale, either no aqueous alkaline relaxant composition would be needed or an aqueous alkaline relaxant composition would be used which contains from about 0.5% to about 1.25% sodium hydroxide.

Regardless of the level of sodium hydroxide in the aqueous alkaline relaxant composition, the composition would only be allowed to remain on the hair for a time of from about 10 minutes to about 30 minutes, preferably for a time of about 15 minutes. After the aqueous alkaline relaxant composition has been allowed to remain on the hair for the desired time, the composition is removed from the hair by rinsing with water. The hair, at this time, can also be shampooed with a non-neutralizing shampoo if necessary to remove any remaining aqueous alkaline relaxant composition from the hair. After rinsing, a non-neutralizing, moisturizing composition is preferably applied to the hair immediately prior to the application of an aqueous waving composition containing a thioglycolate reducing agent. The non-neutralizing moisturizing composition is allowed to remain on the hair during the application of the aqueous waving composition and is rinsed out of the hair along with the aqueous waving composition in a later step. The non-neutralizing moisturizing composition advantageously has a pH of between about 4 and about 6, preferably about 5. The thioglycolate reducing agent in the aqueous waving composition is preferably ammonium thioglycolate. The amount of ammonium thioglycolate in the aqueous waving composition will differ for different types of hair having different natural curl levels. The aqueous waving composition used will advantageously contain from about 0.4% to about 3% ammonium thioglycolate, preferably from about 0.5% to about 2% ammonium thioglycolate, and most preferably, from about 0.5% to about 1.8% ammonium thioglycolate. For more fragile hair types, the aqueous waving composition used would contain from about 0.5% to about 1.5% ammonium thioglycolate. The aqueous waving composition is comprised predominantly of water and includes other ingredients conventionally used in the preparation of cold body wave compositions in addition to the active ingredient, ammonium thioglycolate.

The aqueous waving composition is applied to the hair which is then curled or wrapped onto curling rods. Curling rods, such as permanent wave rods, are made of various materials such as plastic, to not react with the solutions used in the process of the present invention. In addition, curling rods have fastening means that allow the hair to be secured in a desired position about the rod. Curling rods typically vary in diameter with the diameter of the rod selected to give the desired curl diameter to the subject's hair.

After the hair has been rodded, the aqueous waving composition is allowed to remain on the hair for a time of from about 10 minutes to about 30 minutes, preferably for a time of about 15 minutes. The hair is then rinsed thoroughly, while still rodded, to remove all the aqueous waving composition and non-neutralizing moisturizing composition from the hair. After rinsing, a neutralizing composition is applied to the hair on each curling rod and is allowed to remain on the hair for a time of from about 5 minutes to about 13 minutes, preferably for a time of about 10 minutes. The neutralizing composition contains a neutralizing amount of a neutralizing agent selected from the group consisting essentially of hydrogen peroxide, barium chloride, calcium chloride, sodium perborate, potassium perborate, potassium bromate, and sodium bromate. Preferably, the neutralizing agent in the neutralizing compound is sodium bromate. Sodium bromate is a preferred active ingredient in the neutralizing composition because it produces a more springy and tighter curl reformation. In addition, sodium bromate is a stable oxidizing agent which will not decompose as rapidly as other oxidizing agents in storage. The neutralizing composition, which is an aqueous composition, preferably contains from about 5% to about 15% sodium bromate.

After the neutralizing composition has been allowed to remain on the hair for the desired amount of time, the hair is thoroughly rinsed, while still rodded, to remove the neutralizing composition. The curling rods are then removed from the hair and the hair is shampooed with a neutralizing shampoo and rinsed with water. The hair can then be further styled as desired.

While the total process of the present invention is preferably used on virgin hair, the sodium hydroxide formulations of the present invention can be used on hair that has been previously chemically relaxed with a conventional sodium hydroxide-type straightening treatment by applying the appropriate formulation to the new hair growth only, until hair processed by the previous method of relaxation has been all cut off and the new hair treated using the sodium hydroxide treatment portion of the process of the present invention has grown out to the desired length for waving. This is because the bonds in the previously processed hair have been so destroyed that the ammonium thioglycolate would not be effective in imparting a permanent wave pattern to that hair and would only further damage it. Once the previously treated hair has grown out, the whole head of hair is retouched using the total process of this invention, both sodium hydroxide treatment and thioglycolate body waving. All textures of hair must be examined before beginning this process to determine, by reference to the wave balance scale of FIG. 1, what formulation is appropriate for a particular type of hair. This process has been shown to work very well, especially for multi-textured and naturally curly hair; it adds smoothness, a looser permanent wave pattern and weight to the hair, and makes for a much happier client who can now more easily manage his or her hair.

Because multi-textured hair comes from a blend of straight-appearance hair and curly-appearance hair, there are two different problems that must be addressed. The process of the present invention combines the chemicals of both worlds, those used traditionally to straighten the hair of people of African descent and those used to curl Caucasian hair, to get to the desired result of smoothness and control with body and curl.

From the above description it is clear that the process of the present invention is well adapted to carry out the objects and to obtain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

REPRESENTATIVE EXAMPLE

Hair was examined to determine level of curl and type of hair. Sodium hydroxide and ammonium thioglycolate formulations were selected using Wave Balance Scale based on examination of hair.

On virgin hair: The selected sodium hydroxide relaxant formulation was applied to dry hair from ⅛ off scalp to ⅛ to ends in small sections around the head. Each section was smoothed with plastic-gloved hands, although a comb, sponge or other conventional means could have been used. The formulation was allowed to penetrate into the hair cuticle for approximately 15 minutes. The sodium hydroxide formulation was then rinsed from the hair thoroughly with A moisturizing composition having a pH of about 5 was applied to the hair, then the selected ammonium thioglycolate waving formulation was applied to the hair. Both were applied in a conventional manner. The hair was then wrapped (rolled) onto curling rods having a desired size and configuration based on the length of the subject hair. End papers were used in wrapping the hair. The hair was not wrapped too tightly; room was be left for hair expansion and swelling on the rods during processing. After rodding, the waving formulation was allowed to remain on the hair for approximately 15 minutes, with the patron under a plastic cap. The hair was then checked for the desired waved pattern.

The waving formulation was then rinsed from the hair (along with the moisturizing composition) with water while the hair was still rodded. A sodium bromate neutralizing composition was applied to the hair on each rod and was allowed to remain on the hair for about 10 minutes to allow the cysteine bonds in the hair to reform, locking in the new wave pattern. The neutralizing composition was then rinsed from the still rodded hair. Only after neutralization were the rods removed from the hair. The hair was then shampooed with a neutralizing shampoo, rinsed, conditioned, and styled as desired.

In the claims:

1. A process for imparting smoothness and a permanent wave pattern to hair of varying natural curl levels comprising the steps of:

(a) applying an aqueous alkaline relaxant composition, containing an alkaline hydroxide reducing agent to the hair;

(b) allowing said aqueous alkaline relaxant composition to remain on the hair for a time of from about 10 minutes to about 30 minutes, which is sufficient to relax the hair fiber structure without completely straightening the hair;

(c) removing said relaxant composition from the hair by shampooing the hair with a non-neutralizing shampoo and/or rinsing the hair with water;

(d) applying an aqueous waving composition containing a thioglycolate reducing agent to the hair;

(e) rolling the hair onto a plurality of curling rods;

(f) allowing said aqueous waving composition to remain on the rodded hair for a time of from about 10 to about 30 minutes, which is sufficient to rearrange the wave pattern of the hair;

(g) rinsing the rodded hair with water to remove said aqueous waving composition;

(h) applying a neutralizing composition to the rodded hair in an amount and for a time sufficient to lock the wave pattern imparted by said aqueous waving composition into the hair;

(i) rinsing the rodded hair with water to remove said neutralizing composition;

(j) removing the curling rods from the hair; and (k) shampooing and rinsing the hair with a neutralizing shampoo and water.

2. The process of claim 1 further comprising the additional steps, prior to step (a) of:

(i) examining the subject hair using a hair reference scale to determine the type of hair and level of natural curl; and (ii) selecting an aqueous alkaline relaxant composition, containing an alkaline hydroxide reducing agent, and an aqueous waving composition containing a thioglycolate reducing agent appropriate for use on the type of hair and level of curl determined from the hair reference scale.

3. The process of claim 1 wherein said alkaline hydroxide reducing agent is an alkali metal hydroxide.

4. The process of claim 3 wherein said alkali metal hydroxide is sodium hydroxide.

5. The process of claim 1 wherein said aqueous alkaline relaxant composition contains from about 0.5% to about 1.85% sodium hydroxide.

6. The process of claim 1 wherein said aqueous alkaline relaxant composition contains from about 0.5% to about 1.25% sodium hydroxide.

7. The process of claim 1 wherein said aqueous alkaline relaxant composition is allowed to remain on the hair for a time of about 15 minutes.

8. The process of claim 1 including the step of applying a non-neutralizing, moisturizing composition to the hair immediately prior to the application of said aqueous waving composition, allowing the moisturizing composition to remain on the hair during the application of the aqueous waving composition, and rinsing the moisturizing composition out of the hair along with the aqueous waving composition during step (g).

9. The process of claim 8 wherein said non-neutralizing, moisturizing composition has a pH of between about 4 and about 6.

10. The process of claim 9 wherein said non-neutralizing moisturizing composition has a pH of about 5.

11. The process of claim 1 wherein said thioglycolate reducing agent is ammonium thioglycolate.

12. The process of claim 1 wherein said aqueous waving composition contains from about 0.4% to about 3% ammonium thioglycolate.

13. The process of claim 1 wherein said aqueous waving composition contains from about 0.5% to about 2% ammonium thioglycolate.

14. The process of claim 1 wherein said aqueous waving composition contains from about 0.5% to about 1.8% ammonium thioglycolate.

15. The process of claim 1 wherein said aqueous waving composition contains from about 0.5% to about 1.5% ammonium thioglycolate.

16. The process of claim 1 wherein said aqueous waving composition is allowed to remain on the hair for a time of about 15 minutes.

17. The process of claim 1 wherein said neutralizing composition is allowed to remain on the hair for a time of from about 5 minutes to about 13 minutes.

18. The process of claim 17 wherein said neutralizing composition is allowed to remain on the hair for a time of about 10 minutes.

19. The process of claim 1 wherein said neutralizing composition contains a neutralizing amount of a neutralizing agent selected from the group consisting essentially of hydrogen peroxide, chloride or calcium chloride, sodium bromate, sodium perborate, potassium perborate and potassium bromate.

20. The process of claim 19 wherein said neutralizing agent is sodium bromate.

* * * * *